United States Patent [19]

Ohashi et al.

[11] Patent Number: 5,175,088

[45] Date of Patent: * Dec. 29, 1992

[54] RAPID ANALYSIS OF PLURAL COMPONENTS

[75] Inventors: Minoru Ohashi, Nerima; Nobuhiko Arakawa, Shibuya; Osamu Oka, Kawagoe; Kenichi Numazawa, Ageo; Yoshio Utugi, Hiki, all of Japan

[73] Assignees: Oriental Yeast Co. Ltd.; Oriental Electric Co., Ltd., both of Tokyo, Japan

[*] Notice: The portion of the term of this patent subsequent to Feb. 16, 2005 has been disclaimed.

[21] Appl. No.: 616,766

[22] Filed: Nov. 20, 1990

Related U.S. Application Data

[63] Continuation of Ser. No. 118,320, Nov. 9, 1987, abandoned, which is a continuation-in-part of Ser. No. 584,347, Feb. 28, 1984, Pat. No. 4,725,539.

[30] Foreign Application Priority Data

Mar. 8, 1983 [JP] Japan .................. 58-36736

[51] Int. Cl.⁵ .......................... C12Q 1/54; C12Q 1/26; C12Q 1/00
[52] U.S. Cl. .......................................... 435/14; 435/4; 435/18; 435/21; 435/25
[58] Field of Search ............... 435/4, 10, 14, 18, 21, 435/22, 15, 25

[56] References Cited

U.S. PATENT DOCUMENTS

| | | | |
|---|---|---|---|
| 3,879,263 | 4/1975 | Adams | 435/22 X |
| 4,040,908 | 8/1977 | Clark, Jr. | 435/25 X |
| 4,317,878 | 3/1982 | Nakanishi et al. | 435/10 |
| 4,416,982 | 11/1983 | Tsuda et al. | 435/14 X |
| 4,550,078 | 10/1985 | Yamada et al. | 435/25 |
| 4,725,539 | 2/1988 | Ohashi et al. | 435/10 |

FOREIGN PATENT DOCUMENTS

| | | | |
|---|---|---|---|
| 0159513 | 10/1985 | European Pat. Off. | 435/4 |
| 0149050 | 11/1980 | Japan | 435/4 |
| 0097863 | 8/1981 | Japan | 435/22 |
| 0177699 | 11/1982 | Japan | 435/22 |
| 163555 | 9/1984 | Japan . | |
| 2078369 | 1/1982 | United Kingdom | 435/4 |
| 8000454 | 3/1980 | World Int. Prop. O. | 435/25 |

OTHER PUBLICATIONS

Chemical Abstracts, vol. 101, No. 25, Dec. 17, 1984, abstract No. 226,339h, Ohashi et al.
Chemical Abstracts, vol. 96, abstract No. 177337y, (1982) Ima et al.
Chemical Abstracts, vol. 95, abstract No. 38619h, (1981), Tawa et al.
Chemical Abstracts, vol. 98, abstract No. 177577t, (1983), Watanabe et al.
Price et al, "Preparation of Nucleoside Phosphorylase from Calf Spleen" in *Methods In Enzymology*, Colowick et al (edit), vol. II, Academic Press, New York, 1955, pp. 448-453.
Cammann, Karl, *Das Arbeiten mit ionenselectiven Elektroden* (pp. 98-106) Berlin, Heidelberg, New York: Springer-Verlag, 1977.

*Primary Examiner*—Esther L. Kepplinger
*Assistant Examiner*—Toni Scheiner
*Attorney, Agent, or Firm*—Stevens, Davis, Miller & Mosher

[57] ABSTRACT

A new method of rapidly analyzing plural substances in the presence of biological catalyzers is disclosed. The method is practiced by way of the steps of injecting both pH buffer solution and specimen into a reaction cell, successively adding a plurality of enzymes to induce up-take reaction of dissolved oxygen, causing the plurality of substances to be subjected to selective oxidation in the stepwise manner, obtaining a stepdown curve of dissolved oxygen by automatically recording the oxidative process by means of a dissolved oxygen sensor, qualitatively determining each of the substances with reference to the kind of added enzymes and the order of their addition and quantitatively determining the same with reference to the extent of decrease in dissolved oxygen. Typically, oxidation of the substances is carried out by way of two or three or further more steps. The reaction cell for performing the method is equipped with a dissolved oxygen sensor on the one side wall and its upper portion is air-tightly closed with a plug through which a fine bore is formed for the purpose of supply of buffer solution, specimen and enzymes.

5 Claims, 6 Drawing Sheets

△ $d_1$ GLUTAMIC ACID
○ $d_2$ INOSINIC ACID

RAPID ANALYSIS OF PLURAL COMPONENTS

This application is a Continuation of application Ser. No. 118,320, filed Nov. 9, 1987, now abandoned, which is a continuation-in-part of our copending application Serial No. 584,347, filed Feb. 28, 1984, now U.S. Pat. No. 4,725,539.

BACKGROUND OF THE INVENTION

1. Field of the Invention

The present invention relates to a method of rapid analysis of plural components and more particularly to a method of bioelectrochemically analyzing biological substances or foodstuff substances such as amino acids, nucleic acids, saccharides, lipids or the like.

2. Description of the Prior Art

As a typical conventional method of separation analysis on amino acids, nucleic acids, saccharides, lipids, vitamins or the like, chromatographic method has been hitherto employed. However, it is pointed out as drawbacks inherent to the conventional method that it takes long time to separate each of components from one another and moreover a number of reagents and a high level of trained skill are required. Further, another drawback of the conventional method is that an apparatus required for performing the method is complicated in structure and it is manufactured at an expensive cost.

In recent years an improved method of determining only a specific component among plural ones easily, rapidly and selectively with the aid of an electrochemical sensor such as oxygen electrode, hydrogen peroxide electrode with biological catalyzers such as enzyme, biological cell or the like has been proposed (see Koteikakoso, Immobilized Enzymes (1977), edited by Ichiro Chibata and published by Kodansha Scientific Co., Ltd.). However, it is found that the improved method fails to simultaneously analyze plural components.

SUMMARY OF THE INVENTION

Hence, the present invention has been made with the foregoing drawbacks in mind and its object resides in providing a method of simultaneously analyzing plural components rapidly and easily.

To accomplish the above object, there is proposed, in accordance with the present invention, a method of rapidly analyzing plural components essentially comprising the steps of filling pH buffer solution and liquid to be tested into a reaction cell which is designed so as not to allow air to enter therein from the outside, adding plural biological catalyzers one after another, said biological catalyzers being effective for inducing uptake reaction of dissolved oxygen, causing the plural components to be selectively oxidized in the stepwise manner, obtaining a stepdown curve of dissolved oxygen by automatically recording the oxidative process with the aid of a sensor, qualitatively detecting each of the components with reference to the kind of added biological catalyzers and the order of their addition, and quantitatively determining the same with reference to the extent of decrease in dissolved oxygen.

In order to assure that the method of the invention is satisfactorily practiced it is necessary for to provide an apparatus for continuously measuring and recording dissolved oxygen. As a sensor required for the apparatus, any conventional sensors such as polarographic membrane-covered oxygen electrode that is called Clark electrode, galvanic cell type dissolved oxygen electrode, oxygen pressure balancing type oxygen electrode which has been lately invented by Connery or the like sensor is employable.

Further, it is necessary to provide a reaction cell with a dissolved oxygen sensor inserted therein or fitted thereto in which any change of dissolved oxygen in reaction liquid can be exactly measured without any entrance of oxygen from the outside and into which reagent, catalyzer and others can be added as required for the purpose of controlling reaction.

Other objects, features and advantages of the present invention will be more clearly apparent from reading of the following description which has been prepared in conjunction of the accompanying drawings.

BRIEF DESCRIPTION OF THE DRAWINGS

The accompanying drawings will be briefly described below.

DESCRIPTION OF THE PREFERRED EMBODIMENTS

Figure 1:
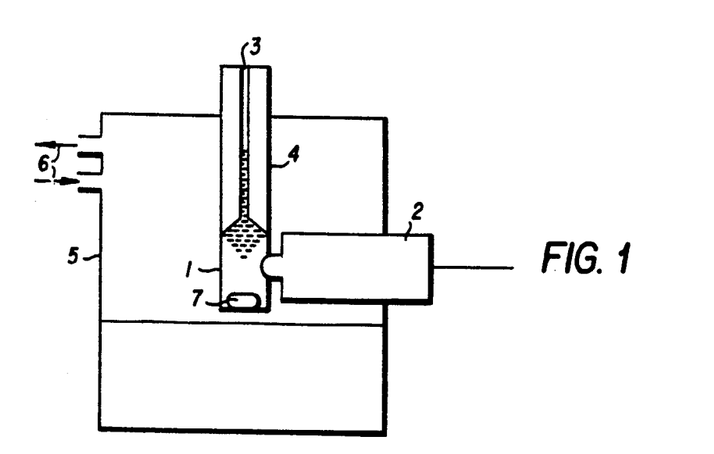
FIG. 1 is a schematic sectional side view illustrating a reaction cell for performing the method of the invention.

In order to readily understand the present invention preferred embodiments will be described below with reference to the accompanying drawings. FIG. 1 schematically illustrates an example of apparatus for performing the method of the invention. The apparatus includes a reaction cell 1 having a capacity of about 2 ml and a dissolved oxygen sensor 2 (hereinafter referred to simply as DO sensor) fixedly secured to the one side wall of said reaction cell 1. Further, the upper part of the reaction cell 1 is airtightly capped with a plug 4 through which a fine bore 3 is provided so that air is prevented from entering the reaction cell 1 from the outside. Thus, a required volume of reaction control agent can be filled into the reaction cell 1 through said fine bore 3 with the aid of a microsyringe or the like device. Reaction temperature is controlled by circulating water 6 throughout the jacket 5 while it is kept at a constant temperature, and reaction liquid is well mixed and stirred with the aid of a magnetic stirrer 7. It should be noted that the present invention should not be limited only to the above-described apparatus and the latter may be changed or modified in any other acceptable manner.

Next, as biological catalyzer for the invention hydrolase such as invertase, amylase or the like and oxidase such as glucose oxidase (hereinafter referred to as G.O.D.) or the like are employable for the purpose of analyzing saccharides, proteases, peptidases and amino acid oxidases are employable for the purpose of analyzing protein and amino acid, and cholesterol esterase and cholesterol oxidase are employable for the purpose of analyzing cholesterol. Further, nucleotidase, nucleosido phosphorylase, xanthin oxidase or the like are employable for the purpose of determining nucleic acid relating substances, for instance, inosinic acid which is obtainable from decomposition of adenosine triphosphate.

It should be noted that dehydrogenase with which there does not occur oxygen uptake reaction, for instance, lactic acid dehydrogenase, alcohol dehydrogenase or the like are employable for analyzing lactic acid, alcohol or the like in the presence of coenzyme and auxiliary agent such as phenazine methasulfate or the like serving as hydrogen transfer agent. In some case biological cell may be employable for the above-mentioned purposes.

Operations for analyzing plural components at the highest efficiency in accordance with the method of the invention can be performed in various manners. As a preliminary step prior to performing the aforesaid operation it is recommendable that reaction characteristics inherent to a single substance among them are previously examined with reference to standard sample, provided that the existence of said substance is known. For instance, conditions for allowing a required oxidation reaction to proceed quickly are confirmed in comparison with slope of oxygen uptake curve while varying quantity of enzyme, pH of reaction solution, composition of buffer solution, temperature and others.

Incidentally, qualitative analysis may be carried out by making determination as to which oxidase and relating biocatalyzers among those added one after another for several substances of which existence is expected is attributable to occurence of oxygen uptake, wherein said determination is assisted by observing whether the oxygen uptake curve is extended downwardly or not.

Since an extent of decrease in output obtained by measurements at two time points corresponds to concentration of a substance which responses to the function of added catalyzer, one of said time points being before said catalyzer is added and the other one being when oxygen uptake reaction (leading to reduction of dissolved oxygen) comes to a stop, quantitative as well as qualitative analysis can be carried out at the same time.

It should be noted that an extent of decrease in output can be converted to a value of dissolved oxygen by obtaining oxygen solubility at a measuring temperature with the aid of a table (for instance, see Section "Dissolved Oxygen" in Testing Method for Industrial Water (JIS K 0101) and Testing Method for Waste Water (JIS K 0102) after a certain buffer solution saturated with air is filled into the reaction cell and output from the sensor is then measured. Thus, an amount of oxygen consumption can be obtained with respect to an unit amount of standard sample by comparing the known concentration of standard sample with an amount of decrease in dissolved oxygen. Accordingly, it is possible to know concentration of the substance immediately from the amount of oxygen consumption without any use of standard solution.

It should be noted that since a substance in which no decrease in dissolved oxygen is recongnized, for instance, sucrose is not subjected to action of glucose oxidase as long as there is provided no preliminary reaction, selection is made for such a preliminary reaction so as to allow invertase which is hydrolase for converting it to reactive one to act on it whereby glucose is produced and it is then oxidized.

Next, the reaction mixture solution of glucose and sucrose is added with enzymes in accordance with the order of glucose oxidase→invertase so that a dissolved oxygen stepdown curve having two steps is obtained. Thus, concentration of glucose can be obtained from the descent extent across the first step, whereas concentration of sucrose can be obtained from the descent extent across the second step. Preliminary reaction as described above may be carried out by way of two steps or three steps or further more steps as required, using hydrolase, transfer enzyme or the like.

Further, a plurality of oxidases may be used for preliminary reaction. Thus, a proper combination of above-described reactions makes it possible to determine a number of substances either qualitatively or quantitatively.

Now, the present invention will be described in more details below with respect to a few examples.

EXAMPLE 1

Analysis of mixed solution of hypoxathin (hereinafter referred to simply as $H_x$) and xanthin (hereinafter referred to simply as X)

1. Principle of the reaction for analysis where reference symbol XO designates xanthin oxidase and reference symbol UO does uricase.

2. Apparatus and material used (1) DO sensor: Clark type electrode which has 3 mm diameter platinum cathode, covered with FEP film having a thickness of 1/1000 inch (manufactured by Oriental Electric Co., Ltd.). When the sensor is in use, 0.7 volt D.C. is applied.

(2) Recorder: It was manufactured by Shimazu Manufacturing Co., Ltd. It had a full scale of 100 mV and it is adapted to operate at a recording rate of 1 cm/min.

(3) Reaction cell: It was controlled to maintain a constant temperature of 37° C. and it had a capacity of 2,000 μ.

(4) Enzyme: XO was used at a rate of 0.4 I.U/ml in the form of 3.2M ammonium sulfate suspension (made by Boehringer Mannheim AG). On the other hand, UO was used at a rate of 0.41 I.U/ml in the form of 50 mM boric acid buffer solution (made by Oriental Yeast Co., Ltd.).

(5) Buffer solusion: It was prepared in the form of 1/15M phosphate buffer solution (pH 7.6) saturated with air at a temperature of 37° C. (P.B.S.). Further, it had concentration of dissolved oxygen of 0.214 μmol/ml (at temperature of 37°C. ).

(6) Liquid to be tested: $H_x$: 10 μmol (1.36 mg)/ml X: 10 μmol (1.52 mg)/ml $H_x$, X: mixture solution of both substances 3. Operations (see FIGS. 2 and 3)

Figure 2:
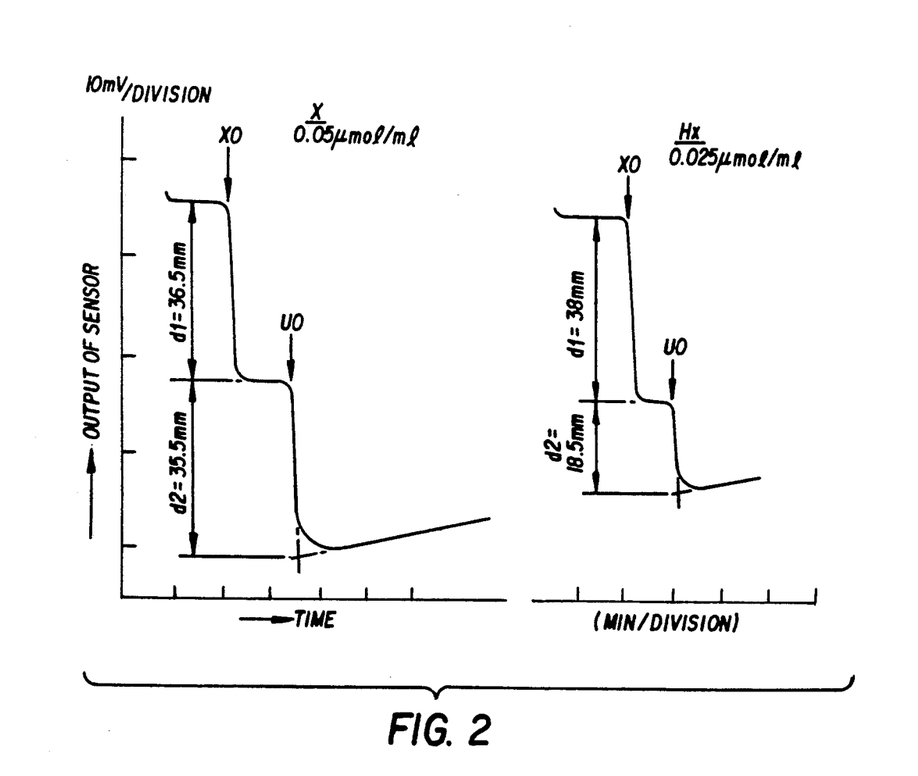
FIG. 2 is a stepdown curve of dissolved oxygen produced during analysis of xanthin (X) and hypoxanthin (Hx).

A volume of appreciably more than 2000 μl of P.B.S. was filled in the reaction cell as illustrated in FIG. 1 and capped with a plug (to such a level that a part of solution was raised upto the lower end of the fine bore 3. Then, liquid of X and $H_x$ to be tested (5 μl or 10 μl in volume) was taken into a microsyringe and thereafter it was injected into the reaction cell through the fine bore 3 while it was stirred. Next, a volume of 20 μl of XO was also injected into the reaction cell and then after it was confirmed by observing a decrease in output of the DO sensor as identified with reference letter $d_1$ in FIG. 2 that the decrease in output from the sensor came to a stop, a volume of 20 μl of UO was added immediately whereby a dissolved oxygen stepdown curve including two steps as illustrated in FIG. 2 was obtained.

Figure 3:
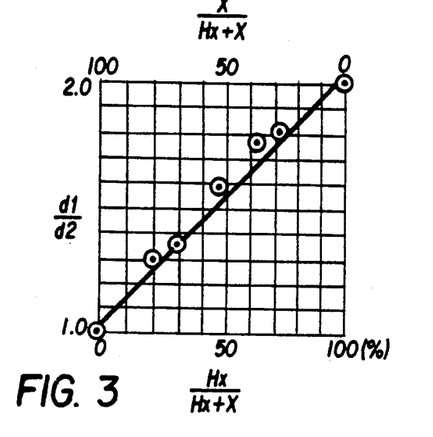
FIG. 3 is a correlation curve illustrating the relation between ratio of xanthin and hypoxanthin concentration and decrease ratio ($d_1/d_2$) in output current generated during oxidative reaction comprising two steps with xanthin oxidase and uricase.

FIG. 3 diagrammatically illustrates a relation between composition ratio of unit liquid to mixed solution and stepdown ratio, that is, $d_1/d_2$. As is apparent from the drawing, stepdown ratio is linearly related to mixing ratio of the mixed solution because the characteristic curve is linearly extended through two points, one of them being such that $d_1/d_2=1$ is established with 100% X and the other one being such that $d_1/d_2=2$ is established with 100% $H_x$.

Incidentally, when a relation between decrease in dissolved oxygen and concentration of substrate was examined, it was found that a volume of oxygen $O_2$ in mol absorbed by addition of UO was related equally to concentration of substrate with respect to either X or $H_x$.

TABLE 1

| Relation between concentration of X and $H_x$ and volume of consumed oxygen $O_2$ | | |
|---|---|---|
| Substrate (composition to be analyzed) in $\frac{\mu mol}{ml}$ | | Volume of absorbed oxygen $O_2$ |
| substance | concentration C during reation | in $\frac{\mu mol}{ml}$ |
| X | 0.05 | 0.054 |
| $H_x$ | 0.25 | 0.028 |

Thus, mol concentration of ($H_x$+X) is obtainable from $d_2$ of the mixture solution of X and $H_x$ and moreover its volume ratio is obtainable with reference to FIG. 3. As a result concentration of each of the substances can be obtained.

Each of the substances is a kind of intermediate metabolite which is excreted in the form of uric acid after decomposition of adenosine triphosphate in animal body and therefore establishment of a method of separating and quantitatively determining them will highly contribute to biochemical industry, foodstuff industry and their associated industries. As is well known, their fractional quantitative determination is achieved only with much difficulties with the aid of any of conventional methods including chromatographic method and conventional enzymatic method (which is normally carried out by optical detection and determination). As will be readily understood from FIG. 2, however, the method of the invention makes it possible to quantitatively determine each of the substances at high accu- racy within a short period of time shorter than 5 minutes without necessity for standard liquid.

EXAMPLE 2

Quantitative determination of substance obtained from decomposition of adenosine triphosphate In this example description will be made as to fractional quantitative determination among inosinic acid (hereinafter referred to simply as IMP), inosine (hereinafter referred to as simply $H_xR$) and hypoxanthin (hereinafter referred to simply as $H_x$).

1. Principle of the reaction for analysis where
reference symbol AP designates alkaline phosphatase,
reference symbol NP does nucleoside phosphorylase,
reference symbol UA does uric acid,
reference symbol Rib does ribose and
reference symbol Pi does inorganic phosphate.

2. Apparatus and material used (1) DO sensor
(2) Recorder
(3) Reaction chamber

The same apparatuses (1) to (3) as those in Example 1 were used for this example under the same operating conditions.

(4) Enzyme

AP was prepared in the form of 3.2M ammonium sulfate suspension and it was used at a rate of 65 I.U/ml (at a temperature of 37° C.).

NP was prepared in the form of 3.2M ammonuium sulfate suspension and it was used at a rate of 20 I.U/ml (at a temperature of 25° C.).

XO was prepared in the form of 3.2M ammonium sulphate suspension and it was used at a rate of 0.4 I.U/ml. each of the enzymes as mentioned above is a product produced by Boehlinger Mannheim AG.

(5) Buffer solution

A liquid was prepared in the form of 1/15M glycine-NaOH buffer solution (having pH 10.5). Further, 2 μl of 0.1M $ZnCl_2$ and 2 μl of 0.1M $MgCl_2$ were added to a volume of 2 ml of A liquid as mentioned above.

B liquid was prepared in the form of 1/15M phosphate buffer solution in the same manner as in the foregoing example.

(6) Liquid to be tested

A volume of 4 μl of mixed solution (10 μmol/ml) comprising IMP, $H_xR$ and $H_x$ each of which was mixed together by the same volumetric rate was used for the experiment.

Figure 4:
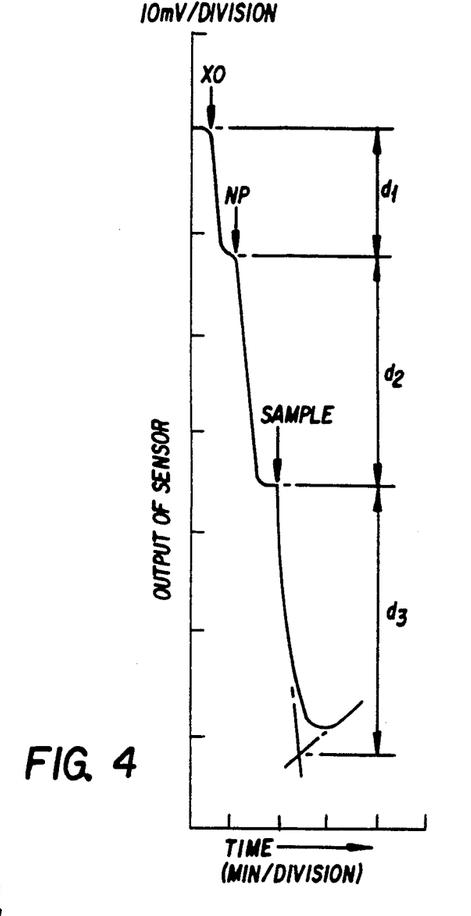
FIG. 4 is a stepdown curve of dissolved oxygen during oxidative reaction comprising three steps for analyzing the mixture liquid of inosinic acid, inosine and hypooxanthin.

3. Operations (see FIG. 4)

Operations can be carried out by way of various types of steps. Now, an example of typical simple process of operations with the minimized quantity of enzyme used therefor will be shown on the following flow sheet.

4. Calculation of concentration $$C_{Hx} = \frac{d_1}{d_0} \times 0.107 \; (\mu mol/ml) \quad (3)$$

$$C_{IMP} = \frac{(d_1 + d_2 - d_3)}{d_0} \times 0.107 \; ('') \quad (4)$$

-continued

$$C_{H_xR} = \frac{(d_3 - d_1)}{d_0} \cdot 0.107 \quad (5)$$

where reference symbol $d_0$ designates recorder span (mm) corresponding to output of water saturated with air and reference symbols $C_{Hx}$, $C_{IMP}$ and $C_{H_xR}$ are the concentrations (μmol/ml) of $H_x$, IMP and $H_xR$.

The principle on which concentration of each of the substances can be obtained from the above-noted calculations will be readily understood on the basis of the reaction formula (2) by any expert in the art, but in view of the fact that each of the substances absorbs oxygen $O_2$ by 2 mol per 1 mol of the former a coefficient of $0.214/2=0.107$ was used for calculations. Since IMP and $H_xR$ do not absorb oxygen in the presence of XO, it will be obvious that $C_{Hx}$ can be obtained with the aid of Equation (3). Next, with respect to reaction corresponding to $d_2$ $C_{(IMP+HxR)}$ can be obtained because $H_x$ has disappeared by addition of XO. Therefore, it results that $(d_1 + d_2)$ corresponds to the number of mol of all substances. Further, with respect to reaction corresponding to $d_3$ initially added substance has disappeared and since the pH is neutral, AP fails to exhibit its activity and therefore substances excluding IMP can be detected. Thus, concentration of IMP can be obtained from difference between $(d_1 + d_2)$ and $d_3$ using Equation (4). Incidentally, no particular description will be required as to calculation of $C_{H_xR}$.

EXAMPLE 3 Quantitative determination of glucose and ethyl alcohol in mixed solution thereof 1. Principle of the reaction for analysis GOD: glucose oxidase
ALOD: alcohol oxidase 2. Apparatus and material used (1) DO sensor:
(2) Recorder:
(3) Reaction cell:

The same apparatus (1) and (2) as those in the preceding examples were used for the present example. However, the apparatus (3) used had a cell volume of 1,080 μl.

(4) Enzyme:

GOD was prepared in the form of white freeze-dried product obtained by extracting and purifying from Aspergillus niger of Type II (made by SIGMA Corporation). The enzyme had activity of 33 Unit (U)/mg. in air saturated solution. Enzyme solution used was prepared by dissolving 5 mg of the powdered enzyme in 1 ml of 0.1M phosphate buffer solution. The so-prepared enzyme solution had activity of 175 U/ml.

ALOD was prepared in the form of yellow freeze-dried product prepared from microorganism (made by TOYO JOZO Co., Ltd.) and had activity of 12 U/mg. Enzyme solution used was prepared by dissolving 35 mg of the powdered enzyme in 1 ml of 0.1M phosphate buffer solution, thus, the solution had activity of 420 U/ml (12×35).

(5) Basal medium for determination:

It was prepared in the form of 0.1M phosphate buffer solution (pH 7.6) (P.B.S.) saturated with air at a temperature of 37° C.

(6) Liquid to be tested:

A. Preparation of glucose solution:

It was prepared in the form of 2.5 mM glucose solution obtained by dissolving 450 mg of anhydrous glucose of reagent grade (made by Kokusan Chemicals Co., Ltd.) in distilled water and filling up it into 100 ml.

B. Preparation of ethyl alcohol (EtOH) solution:

It was prepared in the form of 19 mM ethyl alcohol solution by filling up 290 ul of ethyl alcohol of reagent grade (alcohol content: 99.5%, specific gravity: 0.79) (made by Kokusan Chemicals Co., Ltd.) into 250 ml.

C. Preparation of mixed solution:

It was prepared by filling up each 1 ml of solutions A and B into 10 ml and mixing them together. Thus, the respective components in the so-formed mixed solution had the following concentrations:

Glucose: 25 mM×1/10=2.5 mM
EtOH: 19 mM×1/10=1.9 mM

3. Operations (1) A BOD bottle of 100 ml in volume charged with the basal medium or 0.1M P.B.S. was placed in a thermostat kept at a temperature of 37° C. and air is introduced into the bottle for 5 to 10 minutes by means of an air pump to saturate the basal medium with oxygen.

(2) Water constantly kept at a temperature of 37° C. was flowed through the jacket 6 of the reaction cell shown in FIG. 1 to keep the temperature of the reaction cell constant. Then, the plug 4 was removed and then the basal medium was injected into the reaction cell in an amount (about 1.2 ml) sufficient to allow the liquid surface of the basal medium to reach the lower portion of the fine bore 3. Thereafter, the plug 4 was gently inserted so that any bubble may not remain in the reaction cell.

(3) Output derived from DO reduction current of the DO sensor (2) was recorded on a recording chart of the recorder while rotating the magnetic stirrer 7. A distance $d_0$ between the indication point and DO zero point on the recording chart corresponded to $O_2$ concentration of 0.214 μmol/ml (or 214 μM). (The DO zero point substantially coincides with electrical zero point on the recorder. The DO zero point can be accurately obtained by adding about 100 μl of 0.5M sodium sulfite ($Na_2SO_3$) aqueous solution to the basal medium to complete DO uptake. It is desired to carry out the affirmation of $d_0$ using $Na_2SO_3$ at the initial stage of the determination and after the completion and to use the average value therebetween.)

(4) A microsyringe was fully inserted through the fine bore 3 of the plug 4 of the reaction cell shown in FIG. 1 to inject 20 μl of ALOD into the basal medium.

(5) The liquid to be tested containing the aforementioned amounts of glucose and ethyl alcohol was added to the basal medium by means of another microsyringe while continuing the DO recording. For the purpose of preparing a calibration curve, the liquid to be tested $S_1$ was added in amounts of 5 μl, 10 μl and 20 μl.

Figure 5:
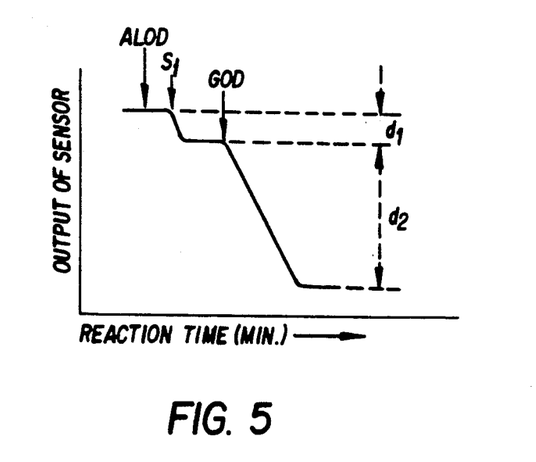
FIG. 5 is a graphical representation showing a step down curve of dissolved oxygen during oxygen uptake reaction by a sample in Example 3.
Figure 6:
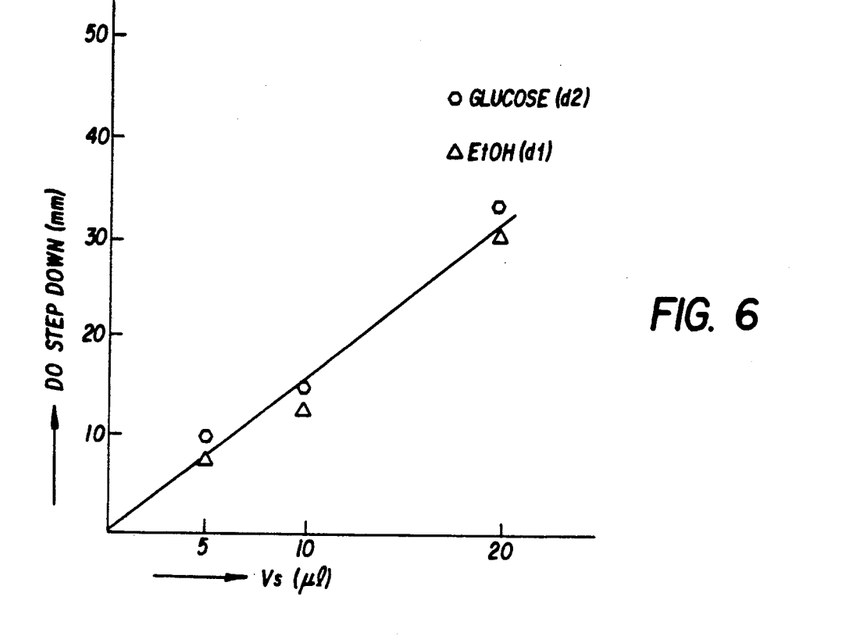
FIG. 6 is a graphical representation showing the relation between DO step down and the injection of a sample in Example 3 which is adapted to be used as a calibration curve for the determination of ethyl alcohol and glucose.

(6) Due to the addition of $S_1$, the recording of a decrease in DO was started at the point indicated by $S_1$ in FIG. 5. This occurred due to the DO uptake or absorption by the basal medium in the reaction cell which was caused with the progress of oxidation reaction or $O_2$ uptake reaction of ethyl alcohol expressed by the above-described reaction formula (6). Such $O_2$ uptake reaction was completed in about 2 minutes. The difference ($d_1$) between the DO value determined before the addition or injection of $S_1$ and that after the completion of the reaction indicates a degree of oxygen uptake of EtOH in the liquid to be tested which was injected to the basal medium. FIG. 6 shows the relation between the amount or volume of addition of the liquid to be tested and DO ($d_1$) step down.

It will thus be understood that the fact that the relation therebetween forms a straight line passing through the zero point that the concentration of EtOH can be determined based on the volume of absorbed or consumed $O_2$.

TABLE 2

Relation between concentration of EtOH and volume of consumed oxygen

| Volume of Sample injected into reaction cell ($\mu l$) | Concentration of EtOH during reaction ($\mu mol/l$) | DO step down ($d_1$) (mm) | Volume of absorbed $O_2$ ($\mu mol/l$) |
|---|---|---|---|
| 5 | 8.75 | 8 | 8.6 |
| 10 | 17.6 | 13 | 13.9 |
| 20 | 35.1 | 31 | 33.3 |

As is apparent from Table 2, the molar ratio of EtOH in the reaction cell to absorbed oxygen is about 1:1, thus, the concentration of EtOH may be calculated the volume of absorbed oxygen without using the calibration curve.

(7) Then, GOD solution of the above-described composition was injected into the basal medium. This caused DO to be decreased again. The reaction was stopped in about 4 to 6 minutes. This was due to the $O_2$ uptake reaction by glucose as indicated by the aforesaid reaction formula (5). Although the molar concentration of absorbed $O_2$ obtained from DO step down was somewhat low as compared with the molar concentration of glucose, the glucose concentration could be obtained from a calibration curve shown in FIG. 6.

Time required to carry out the concurrent determination of EtOH and glucose was as short as 6 to 9 minutes.

TABLE 3

Relation between concentration of glucose and consumed oxygen

| Volume of Sample injected into reaction cell ($\mu l$) | Concentration of glucose during reaction ($\mu mol/l$) | DO step down ($d_2$) (mm) | Volume of absorbed $O_2$ ($\mu mol/l$) |
|---|---|---|---|
| 5 | 11.5 | 10 | 10.8 |
| 10 | 23.1 | 15 | 16.1 |
| 20 | 46.2 | 34 | 36.6 |

Example 4 Quantitative determination of glucose and mono-sodium glutamate (hereinafter referred to as "M.S.G.") in mixed solution thereof 1. Principle of the reaction for analysis $$\beta\text{-D-glucose} + H_2O + O_2 \xrightarrow{GOD} \beta\text{-D-gluconate} + H_2O_2 \quad (5)$$

(The reaction is as in Example 3.)

$$L\text{-glutamate} + O_2 + H_2O \xrightarrow{GLOD} \alpha\text{-ketoglutarate} + H_2O_2 + NH_3 \quad (7)$$

GLOD: glutamate oxidase

2. Apparatus and material used (1) DO sensor
(2) Recorder
(3) Reaction cell

The same apparatus (1) to (3) as those in Example 3 were used for the present example.

(4) Enzyme:

The same GOD as in Example 3 was used. GLOD was used which was made by Research Laboratories, Yamasa Shoyu Co., Ltd. It was prepared in the form of product semi-purified from water extracted solution of wheat bran culture of Streptomyces sp. X-119-6 and had activity of 100 U/ml.

(5) Basal medium for determination

The same basal medium as in Example 3 was used which was 0.1M P.B.S. saturated with air at a temperature of 37° C.

(6) Liquid to be tested

A. Preparation of glucose

The same 2.5 mM glucose solution as in Example 3 was prepared.

B. Preparation of mono-sodium glutamate 0.468 g of mono-sodium glutamate monohydrate (HOOCH-(NH$_2$)CH$_2$CH$_2$COONa H$_2$O) of reagent grade having a molecular weight of 187 (made by Wako Chemicals Co., Ltd.) was filled up into 100 ml using 0.1M P.B.S. to prepare its 25 mM solution

C. Preparation of mixed solution ($S_2$)

Each 1 ml of A and B solutions was filled up into 10 ml using 0.1M P.B.S. Thus, the concentration of each of glucose and sodium glutamate in the so-prepared mixed solution was 2.5 mM.

Figure 7:
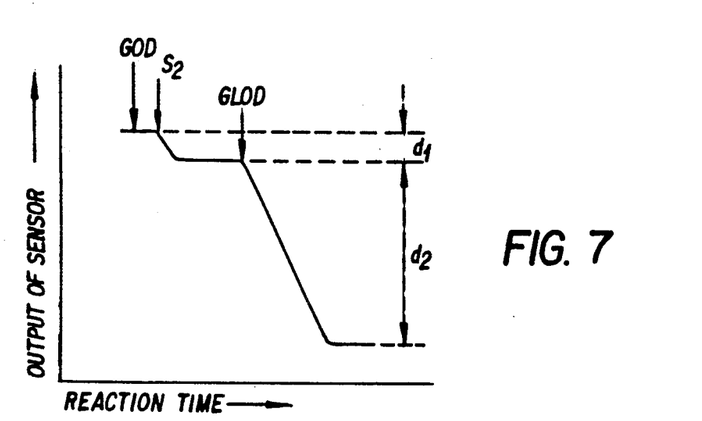
FIG. 7 is a graphical representation showing a step down curve of dissolved oxygen during oxygen uptake by a sample in Example 4.

3. Operations (see FIGS. 7 and 8)

The procedures described in Example 3 were substantially repeated.

The injection of sample solution and enzyme solution was carried out in the following manner.

4. Results

TABLE 4

| Volume of sample ($S_2$) injected into reaction cell ($\mu l$) | Concentration of glucose and glutamic acid during reaction ($\mu mol/l$) | DO step down by GOD | | DO step down by GLOD | |
|---|---|---|---|---|---|
| | | $d_1$ (mm) | Absorbed oxygen ($\mu mol/ml$) | $d_2$ (mm) | Absorbed oxygen ($\mu mol/ml$) |
| 5 | 11.5 | 11 | 11.8 | 8 | 8.6 |
| 10 | 23.1 | 17 | 18.3 | 18 | 19.4 |
| 20 | 46.2 | 40 | 43.0 | 35 | 37.6 |

Figure 8:
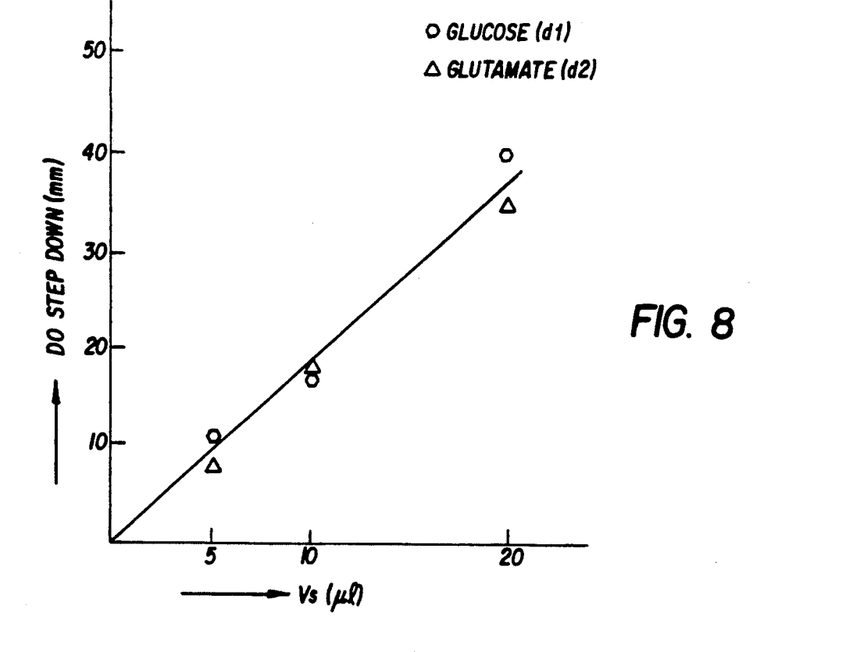
FIG. 8 is a graphical representation showing the relation between DO step down and the injection of a sample in Example 4, which is adapted to be used as a calibration curve for the determination of glucose and glutamic acid.
Figure 9:
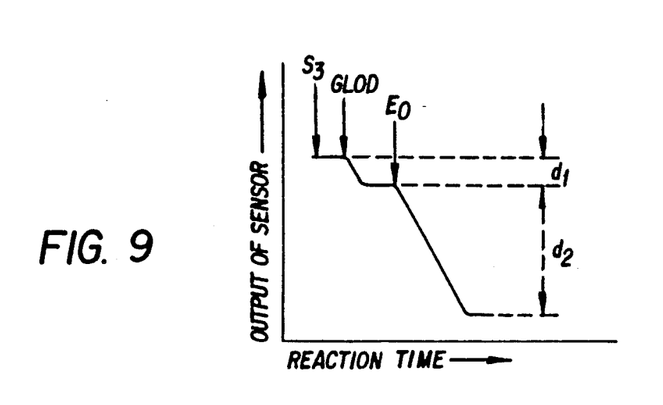
FIG. 9 is a graphical representation showing a step down curve of dissolved oxygen during oxygen uptake by a sample in Example 5.
Figure 10:
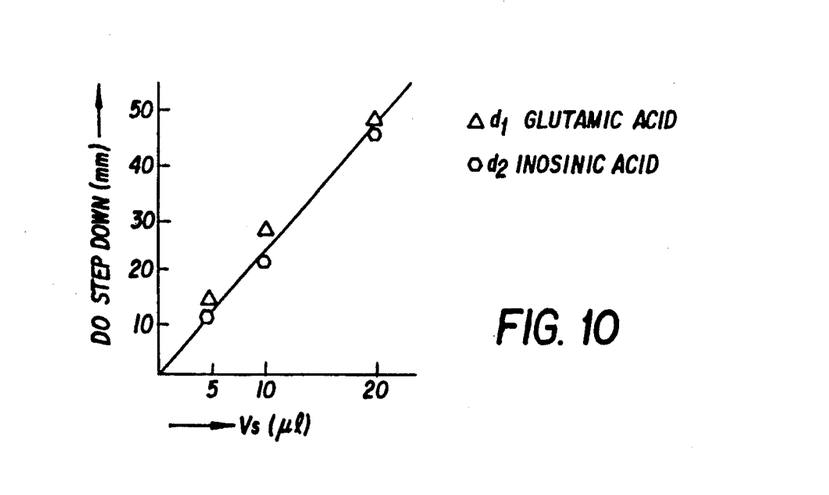
FIG. 10 is a graphical representation showing the relation between DO step down and the injection of a sample in Example 5, which is adapted to be used as a calibration curve for the determination of inosinic acid and glutamic acid.
Figure 11:
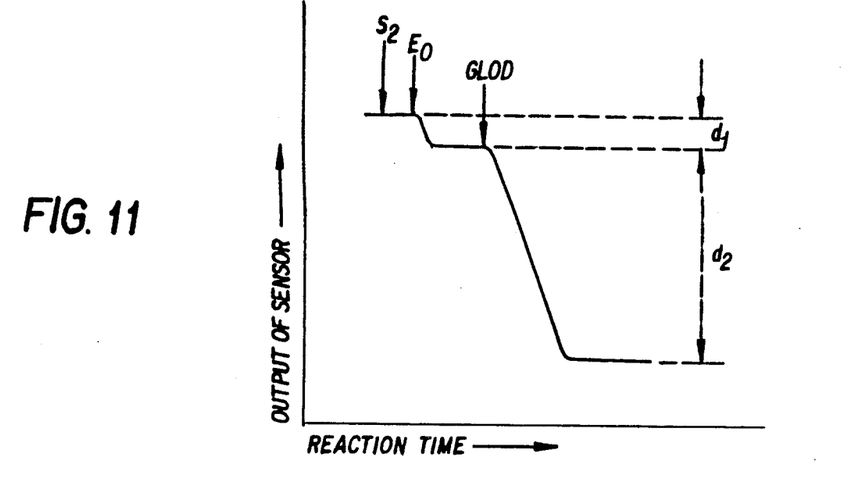
FIG. 11 is a graphical representation showing a step down curve of dissolved oxygen during oxygen uptake by a sample in Example 6.

The recovery of each of glucose and glutamate obtained from the volume of absorbed oxygen was considerably low as compared with the theoretical value of 2.5 mM. However, there is established a linear relation between the injection and $d_1$, $d_2$ as shown in FIG. 8, thus, the concentration of each component can be determined using a calibration curve of FIG. 8.

Example 5

Quantitative determination of inosinic acid and glutamic acid in mixed solution thereof 1. Principle of the reaction for analysis (1mol IMP is equivalent to 2 mol oxygen uptake.)

(1mol glutamate is equivalent to 1mol oxygen uptake.)

2. Apparatus and material used (1) DO sensor
(2) Recorder
(3) Reaction cell

The same apparatus (1) to (3) as those in Example 3 were used for the present example.

(4) Enzyme
AP: 700 U/ml in glycine-NaOH buffer solution of pH 10.5
$E_0$: XO (20 U)+NP (20 U)/ml
GLOD: 100 U/ml. It was used under substantially the same conditions as in Example 4.

(5) Basal medium (Buffer solution)
0.1M phosphate buffer solution of pH 7.6

(6) Liquid to be tested
A. 5'-sodium inocinate (IMP-Na salt) ($C_{10}H_{11}N_4Na_2O_8P \cdot 7H_2O$) (molecular weight: 518)

0.13 g of IMP-Na salt of reagent grade (made by Tokyo Kasei Co., Ltd.) was dissolved in 10 ml of 0.1M P.B.S. to prepare its 25 mM solution.

B. Mono-Na-glutamate $H_2O$ (molecular weight: 187) 25 mM solution was prepared according to the procedures described in Example 4.

C. Preparation of mixed solution 1 ml of A solution and 2 ml of B solution were filled up into 10 ml using 0.1M P.B.S., respectively, to prepare a mixed solution thereof. Thus, the concentrations of the components in the mixed solution were as follows:

Glutamic acid: 25/5=5 mM
IMP: 25/10=2.5 mM

3. Operations (1) Preliminary reaction

80 $\mu l$ of C solution (IMP+Glut) and 80 $\mu l$ of AP enzyme solution were mixed together in a micro-test tube of 2 ml in volume to carry out reaction therebetween at a temperature of 37° C. for 15 minutes, to thereby convert IMP into H$_x$R ($S_2$ solution).

(2) Reaction for determination

The reaction took place according to the following procedures.

4. Results

TABLE 5

| Volume of Sample injected into reaction cell (μl) | Relation between concentration of substrate (inosinic acid and glutamic acid) and volume of oxygen absorbed | | | | | |
|---|---|---|---|---|---|---|
| | Concentration of glutamic acid during reaction (μmol/ml) | DO step down $d_1$ (mm) | Absorbed O by GOD | Concentration of IMP during reaction (μmol/ml) | DO step down $d_2$ (mm) | Absorbed $O_2$ (½) by NP + XO (μmol/ml) |
| 5 | 11.5 | 15 | 16.1 | 5.78 | 11.0 | 5.5 |
| 10 | 23.1 | 28 | 30.1 | 11.5 | 20.5 | 10.25 |
| 20 | 40.2 | 49 | 49.4 | 23.1 | 46 | 23.0 |

The reaction time for determination was 3.5 to 6.5 minutes, and the quantitative value of IMP substantially coincided with the theoretical value.

EXAMPLE 6

Quantitative determination of glutamic acid and inosinic acid in seasoning

1. Principle of the reaction for analysis

The same reactions as in Example 5 took place.

2. Apparatus and material used

The same apparatus (1) to (3) as in Example 5 were used.

The same enzyme (4) and basal medium as in Example 5 were used.

(6) Liquid to be tested 0.5 g of commercially available seasoning powder (made by Ajimonoto Co., Ltd.) was dissolved in 100 ml of P.B.S. to prepare liquid to be tested.

3. Operations (1) Preliminary reaction

80 μl of enzyme solution AP for preliminary reaction was added to 80 μl of $S_1$ solution using a micro-test tube of 2 ml in volume to prepare a mixture and then the so-formed mixture was kept at a temperature of 37° C. for 5 minutes to convert IMP in the sample into $H_xR$ according to the reaction formula (2) ($S_2$ solution).

(2) Reaction for determination

The following procedures were employed for the reaction.

4. Results

TABLE 6

| | | | | Determination of inosinic acid (IMP) and glutamate (Glut) in seasoning | | | | | | |
|---|---|---|---|---|---|---|---|---|---|---|
| Exp. | Vs Volume of sample ($S_2$) injected (μl) | DO step down $d_1$ (mm) | DO step down $d_2$ (mm) | O absorbed in reaction cell (μM) by E | O absorbed in reaction cell (μM) by GLOD | $C_{IMP}$ calculated from O absorbed in reaction cell (μM) | $C_{IMP}$ calculated from O absorbed in reaction cell (mg/l) | $C_{Glut}$ calculated from O absorbed in reaction cell (μM) | $C_{Glut}$ calculated from O absorbed in reaction cell (mg/l) | $C_{IMP} + C_{Glut}$ (mg/l) |
| 1 | 10 | 4 | 126 | 4.45 | 140 | 2.23 | 1.16 | 140 | 26.1 | 27.3 |
| 2 | 10 | 4 | 121 | 4.45 | 134 | 2.23 | 1.16 | 134 | 25.0 | 26.2 |
| mean | 10 | 4 | 124 | 4.45 | 137 | 2.23 | 1.16 | 137 | 25.6 | 26.7 |

$d_0$ = 192 mm
Note 1:
The concentration of IMP ($C_{IMP}$) was obtained according to the following equation based on the fact that the relation of $O_2$ absorption to IMP was 2 mol/1 mol IMP as indicated by the reaction formula (2).
$C_{IMP} = d_1/d_0 \times 0.214/2$ (μmol/ml) = $d_1/d_0 \times 0.107$ (μmol/ml) = $d_1/d_0 \times 107$ (μM)
Note 2:
The concentration of glutamate ($C_{Glut}$) was obtained according to the following equation based on the relation of 1 mol $O_2$/1 mol glutamate.
$C_{Glut} = d_1/d_0 \times 0.214$ (μmol/ml) = $d_1/d_0 \times 214$ (μM)
Note 3:
The concentration by weight/volume of each component was calculated supposing that the molecular weights of IMP and Glut were 518 (heptahydrate) and 187, respectively.
Note 4:
$C_{IMP} + C_{Glut}$ multiplied by 216 which is dilution rate in the process of analysis makes 0.57 g/100 ml, which substantially coincides with the concentration prepared. Also, the ratio of IMP to IMP + Glut is TABLE 6-continued

| | | | | | Determination of inosinic acid (IMP) and glutamate (Glut) in seasoning | | | | | |
|---|---|---|---|---|---|---|---|---|---|---|
| | Vs Volume of sample (S₂) | DO step down | | O absorbed in reaction cell (μM) | | C_IMP calculated from O absorbed in reaction cell | | C_Glut calculated from O absorbed in reaction cell | | C_IMP − C_Glut |
| Exp. | injected (μl) | d₁ (mm) | d₂ (mm) | by E | by GLOD | (μM) | (mg/l) | (μM) | (mg/l) | (mg/l) |

(1.16/26.73) × 100 = 4.3%, which is deemed to indicate correct value. Time required for the analysis was about 10 minutes.

EXAMPLE 7

Quantitative determination of glutamic acid and glucose in soy source.

Soy sauce is Japanese traditional seasoning of which essential components are glutamic acid and glucose.

The prior art fails to readily and rapidly determine such components. The present invention accomplishes the determination of the components for about 10 minutes.

Sample: thick soy sauce (Kikoman Shoyu Co., Ltd.)
1. Principle of the reaction for analysis The same reactions as in Example 4 took place.
2. Apparatus and material used The same apparatus (1) to (3) as in Example 4 were used. Also, the same enzymes (4) and basal medium (5) as in Example 4 were used.

(6) Sample to be tested

Thick soy sauce sold under a trade name "Kikoman Koikuchi Shoyu" from Kikoman Shoyu Co., Ltd. was used.

Preparation of sample solution:

1 ml of the sample was filled up into 100 ml using water to prepare sample solution, and 1 ml to 10 ml of 0.1M phosphate buffer solution was added thereto. Thereafter, the solution was diluted to 1/1000 and saturated with air at a temperature of 37° C. for the analysis.

Figure 12:
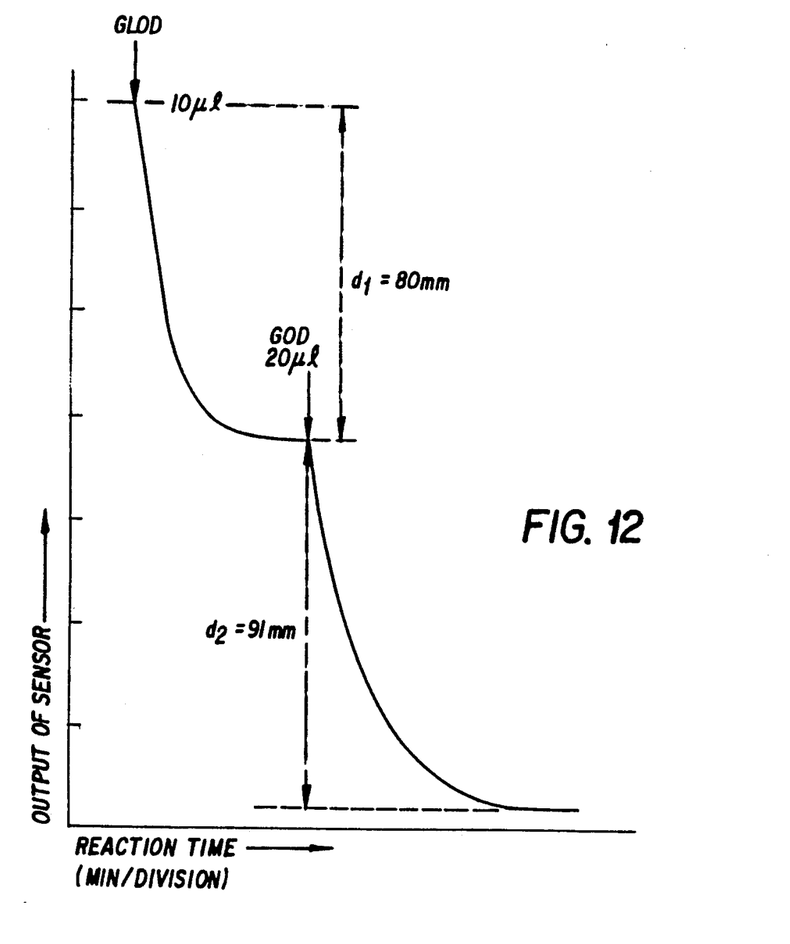
FIG. 12 is a graphical representation showing a step down curve of dissolved oxygen during oxygen uptake by a sample in Example 7.

3. Operations (see FIG. 12 and Table 7)

The following procedures were used for the analysis.

4. Results

TABLE 7

| | | Determination of glutamic acid and glucose in soy source. | | | |
|---|---|---|---|---|---|
| DO step down (mm) | | Absorbed O in cell (μM) | | Content (g/100 ml soy) | |
| d₁ | d₂ | by GLOD | by GOD | C_Glut | C_Glu |
| 80 | 91 | 86.0 | 101.0 | 1.26 | 1.76 | d₀ (in air saturated water) = 199 mm

The calculation was carried out according to the following.

$C_{Glut}$: Concentration of glutamic acid in soy sauce (g/100 ml)

$C_{glu}$: Concentration of glucose in soy sauce (g/100 ml)

$$C_{Glut} = \frac{d_1(mm) \times 0.214(mM) \times 1000(\text{Dilution rate}) \times 147(M.W.)}{d_0(mm)}$$

$$= \frac{80 \times 0.214 \times 1000 \times 147(mg)}{199(l)} = 12.646 \text{ (mg/l)}$$

$$= 1.26 \text{(g glutamic acid/100 ml)}$$

$$C_{glu} = \frac{d_2(mm) \times 0.214(mM) \times 1000 \times 180(M.W.)}{d_0(mm)}$$

$$= \frac{91 \times 0.214 \times 1000 \times 180(mg)}{199(l)} = 17.614 \text{ (mg/l)}$$

$$= 1.76 \text{ (g glucose/100 ml)}$$

EXAMPLE 8

Quantitative determination of L-ascorbic acid(AsA) and glucose in mixed solution thereof 1. Principle of the reaction for analysis $$\text{L-ascorbic acid} + 1/2 O_2 \xrightarrow{ASOD} \text{dehydroascorbic acid} + H_2O \quad (8)$$

$$\beta\text{-D-glucose} + H_2O + O_2 \xrightarrow{GOD} \beta\text{-D-gluconate} + H_2O_2 \quad (2)$$

ASOD: Ascorbate oxidase
GOD: Glucose oxidase

2. Apparatus and material used

The same apparatus (1) and (2) as in Example 5 were used in the present example.

(3) Reaction cell

A reaction cell was used which had a cell volume of 1160 μl and was constructed in substantially same manner as in FIG. 1.

(4) Enzymes

GOD was used which was in the form of yellow freeze-dried product extracted and purified from microorganism (made by Oriental Yeast Co., Ltd.). It had activity of 340 U/mg in $O_2$ saturated solution.

GOD Enzyme solution was prepared by dissolving 5 mg of powdered GOD in 1 ml of 0.1M phosphate buffer solution (pH 7.6). It had activity of 1700 U/ml.

ASOD (made by Oriental Yeast Co., Ltd.) was used which was in the form of white freeze-dried product prepared by purifying enzyme extracted from cucumber. It had activity of 168 U/mg.

ASOD enzyme solution was prepared by dissolving powdered ASOD enzyme in 0.1M calcium phosphate buffer solution containing 1 mg/ml of albumin as stabilizer at a rate of 1 mg/ml. It had activity of 168 U/ml.

(5) Basal medium for determination 0.1M phosphate buffer solution (P.B.S.) (pH 7.6) was used which was saturated with air at a temperature of 30° C.

(6) Liquid to be tested

A. Preparation of ascorbic acid (AsA)

10 mM ascorbic acid solution was prepared by dissolving 176 mg of L-ascorbic acid of reagent grade (made by Wako Pure Chemical Industries, Ltd.) in 100 ml of 2% $HPO_3$ solution and kept in a refrigerator. The solution was diluted to a desired degree prior to use. ($HPO_3$ is a stabilizer of AsA.)

B. Preparation of glucose solution 25 mM glucose solution was prepared by dissolving 450 mg of anhydrous glucose (made by Kokusan Chemicals Co., Ltd.) in distilled water and then filling up it to 100 ml.

C. Preparation of mixed solution 1 ml of A solution and 0.4 ml of B solution were mixed together to prepare a mixture and and then the so-formed mixture was filled up into 2 ml using distilled water.

Thus, the concentrations of the components in the mixed solution were as follows:

$AsA \cdots 10\ mM \cdot \frac{1}{2} = 5\ mM$ $Glucose \cdots 25\ mM \times 1/5 = 5\ mM$ 3. Operations (1) 100 ml BOD bottle filled with the basal medium or 0.1M PBS was placed in a thermostat kept at a temperature of 30° C. and air was introduced into the bottle for 20 minutes by means of an air pump.

(2) Water kept at 30° C. was flowed through a jacket of the reaction cell to constantly maintain the reaction cell at 30° C. Then, a plug was removed from the reaction cell and the basal medium saturated with air was injected into the reaction in an amount of 2 ml to reach the lower portion of a fine bore. Thereafter, the reaction cell was capped with the plug in a manner to prevent any bubble from remaining in the reaction cell.

(3) Output derived from DO reduction current of the DO sensor was recorded on a record chart of the recorder while rotating a magnetic stirrer in the reaction cell. Distance $d_o$ between the indication point and DO zero point corresponded to $O_2$ concentration of 0.235 μmol/ml (at 30° C.).

(4) A microsyringe was deeply inserted into the fine bore of the reaction cell to inject 20 μl of ASOD into the cell.

(5) The liquid to be tested containing ascorbic acid and glucose was injected by means of another syringe while continuing the DO recording. For the purpose of preparing a calibration curve, the liquid was injected in amounts of 10 μl, 20 μl and 30 μl.

Figure 13:
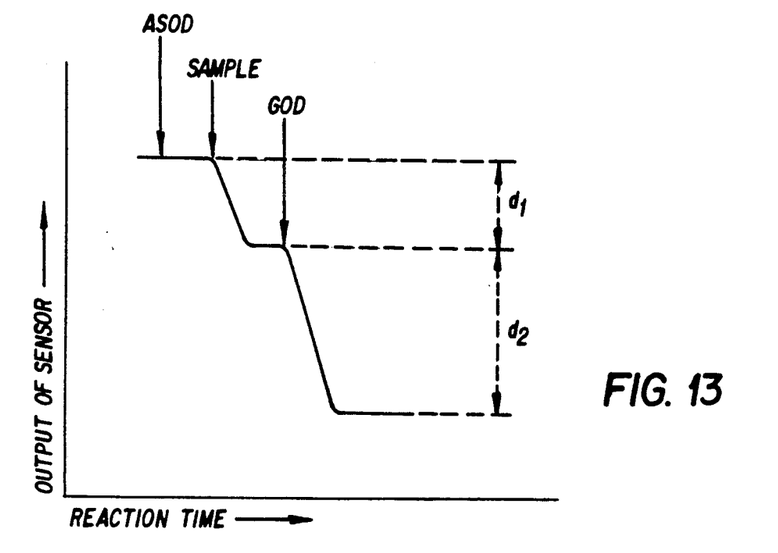
FIG. 13 is a graphical representation showing a step down curve of dissolved oxygen during oxygen uptake by a sample in Example 8.

(6) A decrease in DO due to the injection of sample was recorded which was initiated at the point indicated by sample in FIG. 13. This was owing to the absorption of DO by the basal medium in the reaction cell which occurred with the progress of $O_2$ uptake reaction by ascorbic acid indicated by reaction formula (1). The reaction was completed in about 1 minute. The so-obtained difference $d_1$ between DO prior to the injection of ASOD and DO upon completion of the reaction indicates $O_2$ uptake by the liquid to be tested.

Figure 14:
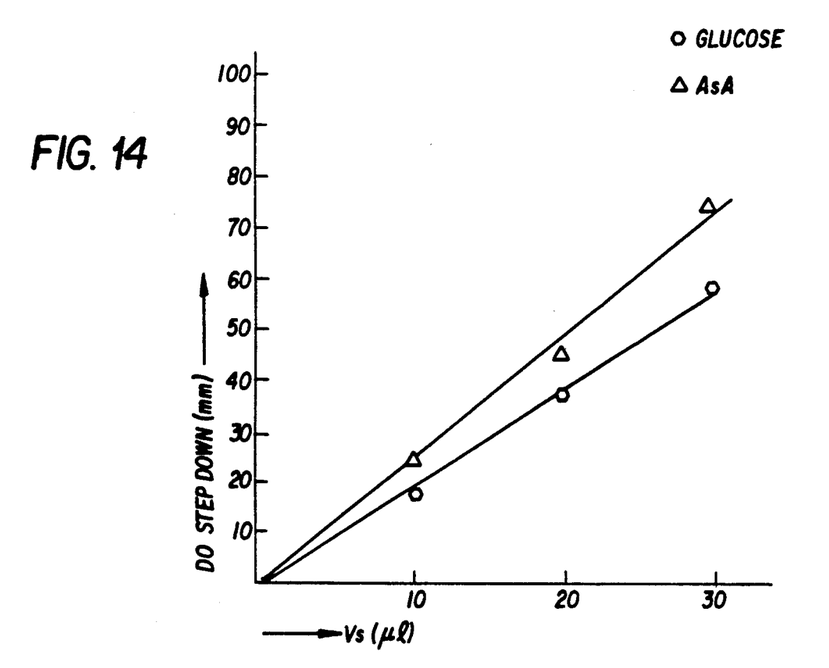
FIG. 14 is a graphical representation showing the relation between DO step down and the injection of a sample in Example 8, which is adapted to be used as a calibration curve for the determination of ascorbic acid and glucose.

FIG. 14 shows the relationship between the injection of liquid to be tested and DO step down.

TABLE 8

Relation between concentration of AsA and volume of consumed oxygen

| Volume of sample injected into reaction cell $V_s$ (μl) | Concentration of AsA during reaction (μmol/l) | DO step down ($d_1$) (mm) | Volume of absorbed $O_2$ (μmol/l) |
| --- | --- | --- | --- |
| 10 | 43.0 | 18 | 21.4 |
| 20 | 86.0 | 38 | 45.1 |
| 30 | 129.0 | 58 | 68.8 |

(7) Thereafter, the injection of GOD solution in amount of 20 μl caused a decrease in DO again. The reaction was completed in 4 to 6 minutes.

The concurrent determination of AsA and glucose described above required time as short as 5 to 7 minutes.

TABLE 9

Relation between concentration of glucose and volume of consumed oxygen

| Volume of sample injected into reaction cell $V_s$ (μl) | Concentration of glucose during reaction (μmol/l) | DO step down ($d_1$) (mm) | Volume of absorbed $O_2$ (μmol/l) |
| --- | --- | --- | --- |
| 10 | 43.0 | 25 | 29.7 |
| 20 | 86.0 | 46 | 54.6 |
| 30 | 129.0 | 75 | 89.0 |

As can be seen from Tables 8 and 9, $O_2$ uptakes by AsA and glucose are somewhat less than the theoretical values obtained by the reaction formula (8) and (2). However, as shown in FIG. 14, each of the components has a linear relation between $O_2$ uptake and the concentration which forms a straight line passing through the origin. Thus, it will be noted that the concurrent determination of ascorbic acid and glucose is carried out using a calibration curve shown in FIG. 18.

The process of the present invention can readily and effectively determine plural components, for example, such as lipids, amino acids, materials relating to nucleic acids, alcohols, vitamins and the like which are contained in food, drink and organism and the like without separating the components from one another by a highly simple process comprising the steps of progressively adding oxidases for the respective components to the sample solution to cause oxygen uptake by the components and rapidly determining the oxygen uptake by means of an electrochemical sensor.

Various kinds of methods for determining components in organism have been conventionally proposed which use oxidase. However, the conventional methods each are adapted to determine only one specific component. In order to avoid such a disadvantage, it would be conceived to utilize a plurality of sensors according to an immobilized enzyme sensor system. However, such a system causes an apparatus to be highly complicated in structure, so that it may not be substantially put to practical use.

The present invention can be readily practiced using a simple apparatus having a single sensor installed therein and is capable of determining a number of components for a short period of time only by suitably setting some conditions such as kinds of enzymes to be used, the order of addition or injection of the enzymes, preliminary reaction and the like. Thus, it will be readily understood that the present invention can be positively put to practical use.

For example, the analytical process described in Example 2 is effectively applicable to rapid determination of freshness index (so called K value) of meat, fish or the like which attracts much attention now.

The determination of K value by a chromatographic method requires time as long as 3 to 6 hours. On the contrary, the present invention readily and rapidly accomplishes the determination for a significantly short period of time such as several minutes.

Also, the present invention is adapted to allow the determination be expressed in the form of current which is proportional to the amount of chemical species, thus, it can be practiced using a computer system. For example, the determination of K value may be graphically displayed using a computer.

Finally, features and advantages of the present invention will be summarized below.

(1) Preliminary treatment is easy to be carried out for specimen without any influence of coloring, turbidity, absorbability of ultraviolet ray and others of liquid to be tested.
(2) Measurements are made very rapidly.
(3) Excellent high specificity is assured.
(4) An apparatus for practicing the method can be designed very simply.
(5) Measurements can be made at a low concentration in the range of 0.005 to 0.1 μmol/ml with excellent high sensibility.
(6) A quantity of consumption of enzyme can be minimized by using a small reaction cell. As described in Example 2, enzyme which has once added can be used repeatedly (for instance, XO can be used three times and NP can be used two times).
(7) All operations are performed at a room temperature with high safety because of no necessity for dangerous chemicals.

As will be readily understood from the above description, the method of the present invention has many adventageous features as noted above and therefore it very useful for analysis of various substances as mentioned above.

While the present invention has been described above only with respect to typical embodiments and examples, it should of cource be understood that it should not be limited only to them but various changes or modifications may be made without any departure from the spirit and scope of the invention.

What is claimed is:

1. A method for analyzing glucose and ethyl alcohol in a liquid containing them, which comprises the steps:
    (a) adding a volume of the liquid and a pH buffer solution to a reaction cell designed to prevent air from entering the cell, said reaction cell being equipped with an oxygen sensor connected to an automatic recording device,
    (b) adding an enzyme selected from the group consisting of glucose oxidase and alcohol oxidase to the liquid which catalyzes oxidation of one component in the liquid,
    (c) continuously recording oxygen sensor output,
    (d) adding an enzyme selected from the group consisting of glucose oxidase and alcohol oxidase which is different from the enzyme added in step (b) to the liquid which catalyzes oxidation of a second component in the liquid,
    (e) continuously recording oxygen sensor output, and
    (f) calculating the amount of said one component of step (b) from the decrease in oxygen sensor output in step (c) and calculating the amount of said second component present in the liquid from the decrease in oxygen sensor output in step (e).

2. A method for analyzing glucose and mono-sodium glutamate in a liquid containing them, which comprises the steps:
    (a) adding a volume of the liquid and a pH buffer solution to a reaction cell designed to prevent air from entering the cell, said reaction cell being equipped with an oxygen sensor connected to an automatic recording device,
    (b) adding an enzyme selected from the group consisting of glucose oxidase and glutamic acid oxidase to the liquid which catalyzes oxidation of one component in the liquid,
    (c) continuously recording oxygen sensor output,
    (d) adding an enzyme selected from the group consisting of glucose oxidase and glutamic acid oxidase which is different from the enzyme added in step (b) to the liquid which catalyzes oxidation of a second component in the liquid,
    (e) continuously recording oxygen sensor output, and
    (f) calculating the amount of said one component of step (b) from the decrease in oxygen sensor output in step (c) and calculating the amount of said second component present in the liquid from the decrease in oxygen sensor output in step (e).

3. A method for analyzing inosinic acid and glutamic acid in a liquid containing them, which comprises the steps:
    (a) adding a volume of the liquid and a pH buffer solution to a reaction cell designed to prevent air from entering the cell, said reaction cell being equipped with an oxygen sensor connected to an automatic recording device,
    (b) adding xanthene oxidase and an enzyme selected from the group consisting of nucleoside phosphorylase and glutamic acid oxidase to the liquid,
    (c) continuously recording oxygen sensor output,
    (d) adding an enzyme selected from the group consisting of nucleoside phosphorylase and glutamic acid oxidase which is different from the enzyme added in step (b) to the liquid which catalyzes oxidation of a second component in the liquid,
    (e) continuously recording oxygen sensor output, and
    (f) calculating the amount of said one component of step (b) from the decrease in oxygen sensor output in step (c) and calculating the amount of said second component present in the liquid from the decrease in oxygen sensor output in step (e) provided that when nucleoside phosphorylase is the added enzyme alkaline phosphatase is added together with the nucleoside phosphorylase.

4. A method for analyzing glutamic acid and glucose in a liquid containing them, which comprises the steps:
(a) adding a volume of the liquid and a pH buffer solution to a reaction cell designed to prevent air from entering the cell, said reaction cell being equipped with an oxygen sensor connected to an automatic recording device,
(b) adding an enzyme selected from the group consisting of glutamic acid oxidase and glucose oxidase to the liquid which catalyzes oxidation of one component in the liquid,
(c) continuously recording oxygen sensor output,
(d) adding an enzyme selected from the group consisting of glutamic acid oxidase and glucose oxidase which is different from the enzyme added in step (b) to the liquid which catalyzes oxidation of a second component in the liquid,
(e) continuously recording oxygen sensor output, and
(f) calculating the amount of said one component of step (b) from the decrease in oxygen sensor output in step (c) and calculating the amount of said second component present in the liquid from the decrease in oxygen sensor output in step (e).

5. A method for analyzing ascorbic acid and glucose in a liquid containing them, which comprises the steps:
(a) adding a volume of the liquid and a pH buffer solution to a reaction cell designed to prevent air from entering the cell, said reaction cell being equipped with an oxygen sensor connected to an automatic recording device,
(b) adding an enzyme selected from the group consisting of ascorbate oxidase and glucose oxidase to the liquid which catalyzes oxidation of one component in the liquid,
(c) continuously recording oxygen sensor output,
(d) adding an enzyme selected from the group consisting of ascorbate oxidase and glucose oxidase which is different from the enzyme added in step (b) to the liquid which catalyzes oxidation of a second component in the liquid,
(e) continuously recording oxygen sensor output, and
(f) calculating the amount of said one component of step (b) from the decrease in oxygen sensor output in step (c) and calculating the amount of said second component present in the liquid from the decrease in oxygen sensor output in step (e).

* * * * *